United States Patent [19]

Yaniv et al.

[11] Patent Number: 4,904,235

[45] Date of Patent: Feb. 27, 1990

[54] DIALYSIS BAG HOLDING DEVICE

[75] Inventors: Avraham Yaniv; Arnona Gazit, both of Holon, Israel

[73] Assignee: Bel-Art Products, Inc., Pequannock, N.J.

[21] Appl. No.: 151,949

[22] Filed: Feb. 3, 1988

[51] Int. Cl.⁴ .............................................. A61F 2/16
[52] U.S. Cl. ............................................. 604/6; 127/54; 210/249; 248/94; 248/95; 248/100
[58] Field of Search ............... 210/249, 513, 644–655, 210/321; 248/94, 95, 99, 100, 101; 604/6, 29; 127/10, 54; 204/138

[56] References Cited

U.S. PATENT DOCUMENTS

| | | | |
|---|---|---|---|
| 473,081 | 4/1892 | Rahn | 210/249 |
| 603,323 | 5/1898 | Eckart | 210/249 |
| 1,208,882 | 12/1916 | Young | 210/249 |
| 1,536,890 | 5/1925 | Lagemann | 210/249 |
| 1,742,078 | 12/1929 | Jacobs | 248/94 |
| 2,149,722 | 3/1939 | Blanchard | 248/94 |
| 2,397,902 | 4/1946 | McDill | 210/249 |
| 2,905,418 | 9/1959 | Escartin | 210/249 |
| 3,095,578 | 7/1963 | Stanford | 248/99 |
| 3,679,125 | 2/1972 | Forance et al. | 248/99 |
| 3,818,956 | 6/1974 | Chamberlain | 248/99 |
| 4,248,278 | 2/1981 | Blodgett | 248/99 |
| 4,485,855 | 12/1984 | Dillingham | 248/99 |
| 4,560,475 | 12/1985 | Kataoka | 210/249 |
| 4,640,188 | 2/1987 | Joyner | 210/513 |

FOREIGN PATENT DOCUMENTS

| | | | |
|---|---|---|---|
| 60688 | 4/1891 | Fed. Rep. of Germany | 210/249 |
| 873831 | 3/1953 | Fed. Rep. of Germany | 210/249 |
| 67078 | 10/1913 | Switzerland | 210/249 |
| 713894 | 8/1954 | United Kingdom | 210/249 |

Primary Examiner—Max Hindenburg
Assistant Examiner—K. M. Reichle
Attorney, Agent, or Firm—Anthony F. Cuoco

[57] ABSTRACT

A device for holding dialysis bags includes a hollow funnel-like member for holding dialysis bags of various sizes. A hanger arrangement extends from the funnel-like member, whereby said member carrying a dialysis bag may be suspended within a vessel or the like without additional support. A cap is secured to the funnel-like member to seal said member.

6 Claims, 1 Drawing Sheet

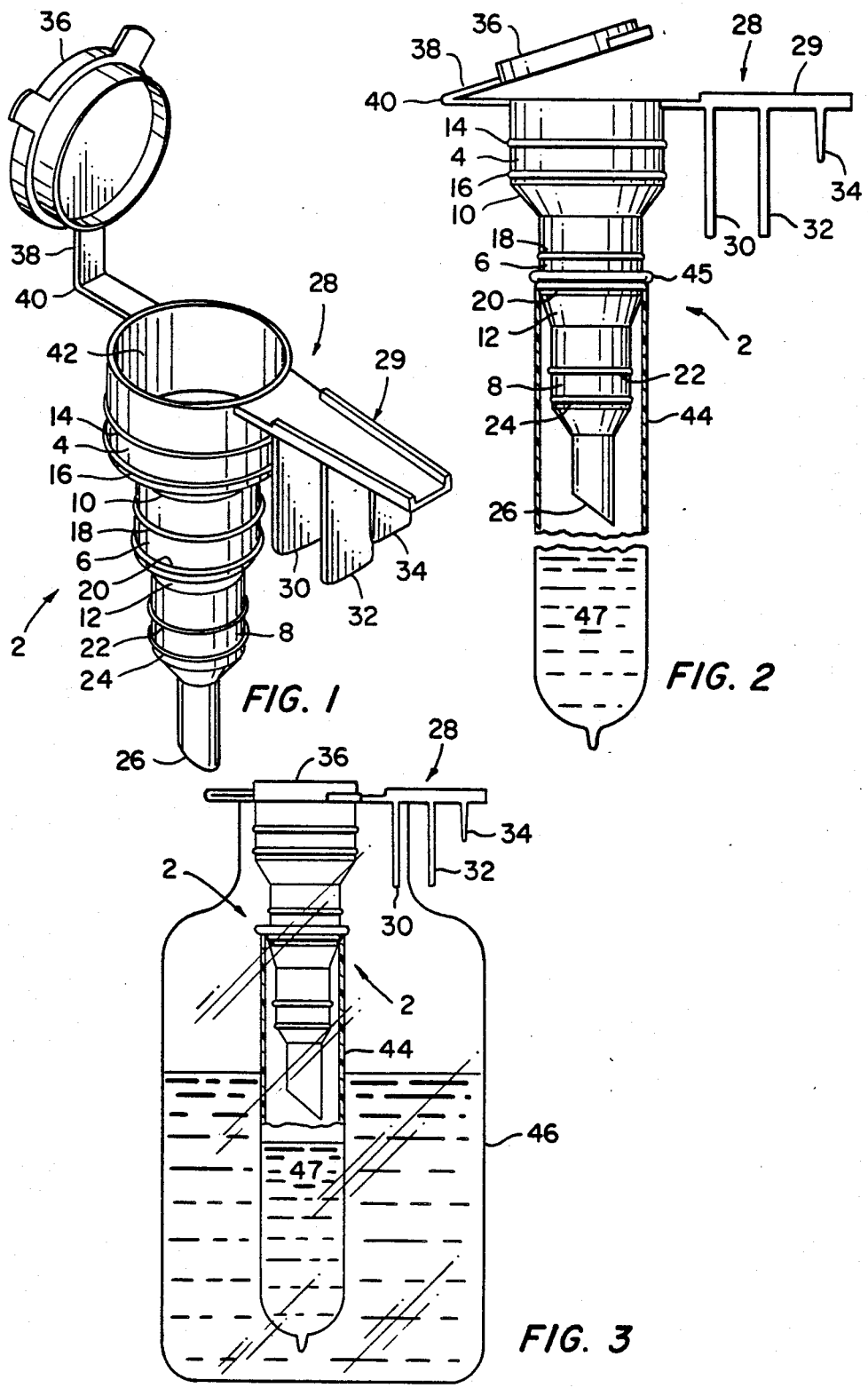

DIALYSIS BAG HOLDING DEVICE

BACKGROUND OF THE INVENTION

Dialysis is defined as the separation of substances in solution by means of their unequal diffusion through a semi-permeable membraneous member such as, for example, the separation of colloids from soluble substances. Dialysis as defined has many applications in both the commercial and health allied fields. An example of the former is the recovery of sodium hydroxide in the manufacture of viscose. An example of the latter is in blood fractionation. The substance that passes through the membraneous member is called the dialysate.

In handling subtance samples for dialysis it is necessary to transfer the sample to and from the membraneous member, commonly known as a "dialysis bag." When using dialysis in the health allied fields it is imperative that the dialysis process be conducted under sterile conditions. Accordingly, the present invention relates to a new and novel device for holding dialysis bags to accomodate these conditions.

SUMMARY OF THE INVENTION

This invention contemplates a device for holding dialysis bags including a funnel-like member having a plurality of longitudinally extending annular sections of decreasing diameters for holding dialysis bags of a corresponding plurality of sizes. A hanger arrangement extends substantially normal to the funnel-like member, whereby said member is adapted to be suspended in vessels having openings of variou sizes. A cap is secured to the funnel-like member via a strap. With the arrangement described a substance for dialysis can be transferred to the dialysis bag through the funnel-like member, after which the member is capped and suspended in a vessel for dialysis. The contents of the dialysis bag (the dialysate) can be easily emptied by uncapping the device and pouring said contents into a receiving container, or by using a conventional pipette or the like to accomplish same. The invention contemplates molding the device out of a suitable plastic material such as polypropylene whereby a unitary dialysis bag holding device is provided.

BRIEF DESCRIPTION OF THE DRAWING

FIG. 1 is a perspective representation of the device of the invention.

FIG. 2 is a side elevational view of said device showing a partially sectioned dialysis bag attached thereto.

FIG. 3 is a side elevational view of said device showing a partially sectioned dialysis bag attached thereto and suspended in a vessel for dialysis.

DETAILED DESCRIPTION OF THE INVENTION

With reference first to FIG. 1, the device for holding a dialysis bag disclosed herein includes a hollow funnel-like member 2. Funnel-like member 2 includes a plurality of longitudinally extending annular sections of decreasing diameters, shown as three in number and designated by the numerals 4, 6 and 8. Section 4 is connected to section 6 via a frusto-conical section 10 and section 6 is connected to section 8 via a frusto-conical section 12.

Section 4 carries at least two circumferential outwardly projecting rings 14 and 16 near the center and the bottm of the section respectively; section 6 carries at least two circumferential outwardly projecting rings 18 and 20 near the center and the bottom of the section, respectively and section 8 carries like rings 22 and 24 near the center and the bottom of the section, respectively. Section 8 terminates in a stem 26.

A hanger 28 extends from the top of funnel-like member 2 and includes an arm 29 substantially normal to the axis of member 2. Arm 29 carries a plurality of fingers 30, 32 and 34 along the length thereof and substantially normal thereto, said fingers being in spaced relation to each other. Fingers 30, 32 and 34 may be of different lengths to satisfy the purposes of the invention as will become evident.

A cap 36 is secured to funnel-like member 2 via a strap or the like 38 attached to the cap and to the top of funnel-like member 2. Strap 38 has a center section 40 which is thinner than the ends of the strap so as to form a hinge, whereby cap 36 is displaced toward and away from an opening 42 extending through funnel-like member 2 to open and close the member for purposes which will hereinafter become evident.

With reference to FIG. 2, a semi-membraneous dialysis bag is designated by the numeral 44. Dialysis bag 44 is attached to funnel-like member 2 by disposing the dialysis bag over an appropriate one of the annular sections 4, 6 or 8, such as section 6 shown in the Figure. Dialysis bag 44 is urged over one of the rings on the annular section such as ring 20, and secured to the annular section via a rubber band or the like 45.

The substance for dialysis (the dialysate), designated by the numeral 47 is transferred to bag 44 by pouring said substance into funnel-like member 2, whereupon the substance flows into the bag. The contents of the dialysis bag may be emptied by pouring the material through the funnel-like member or by inserting a pipette through the funnel into the dialysis bag. With the substance 47 in the bag, funnel-like member 2 is capped via cap 36 and the funnel-like member with dialysis bag 44 attached thereto is suspended for dialysis as will be next described.

With reference to FIG. 3, funnel-like member 2 with dialysis bag 44 attached thereto as aforenoted, is suspended in a suitable vessel which may be a jar or a beaker or such other like container, and designated by the numeral 46. The arrangement is such that the edge of the neck of container 46 is disposed between spaced hanger fingers such as 30 and 32, so that the bag may be suspended in the container without assistance or other support. With the arrangement shown hanger 28 is universal in nature for convenient dialysis in containers having necks or openings of various sizes.

It will now be recognized that a new and unique device specifically designed to facilitate handling of dialysis bags has been provided by the present invention. Funnel-like member 2 is adaptable for holding a variety of sizes of dialysis bags and it is ideal for handling samples for dialysis under strict sterile conditions. Moreover the device is readily adaptable for introducing gel strips for electroelution, as may be desired.

Cap 36 in the described arrangement provides a seal for funnel-like member 2 via a simple snap-in arrangement. The top of cap 36 may have a textured surface to provide a writing area for dialysis sample identification.

Finally, the construction of the device described renders it usable in a disposable mode or in a re-usable autoclavable mode, as may be desired.

The invention contemplates in its preferred embodiment a unitary device molded of a suitable plastic material such as polypropylene, wherein funnel-like member 2, hanger 28, cap 36 and strap 40 are integral with each other as will now be understood.

Although the invention has been described and shown with reference to outwardly projecting rings 14, 16, 18, 20, 22, 24 to aid in retaining dialysis bag 44 on funnel-like member 2, said rings may not be necessary in some applications and may therefore be omitted.

With the aforenoted description of the invention in mind reference is made to the claims appended hereto for a definition of the scope of the invention.

What is claimed is:

1. A dialysis device, comprising:
   a plurality of different-sized dialysis bag means for receiving dialysate, each of said bag means including an open end and a closed end;
   a plurality of dialysis vessel means for receiving said different-sized bag means, said plurality of vessel means including openings of different sizes, respectively;
   a hollow funnel-like member including a plurality of annular sections of different diameters coaxially connected to each other in order of progressing diameter, the annular section of smallest diameter defining a first open end and the annular section of greatest diameter defining an opposite second open end;
   each of the annular sections for disposition of a dialysis bag means of a different size thereon and including a plurality of exterior, radially projecting, circumferential rings in axially spaced relation to each other;
   the open end of the dialysis bag means of desired size being passed over the first open end of the funnel-like member and disposed on the annular section of appropriate diameter extending over one of the rings thereon;
   means for securing the desired-size dialysis bag means disposed on the appropriate annular section to the funnel-like member;
   hanger means supported by the funnel-like member for suspending the funnel-like member from the opening of one of said plurality of dialysis vessel means, with the closed end of the dialysis bag means disposed thereon extending into the one vessel means; and
   means for capping the second open end of the funnel-like member.

2. A device as described by claim 1, wherein the hanger means includes:
   an arm supported by the funnel-like member adjacent the second open end thereof and extending substantially normal with respect to the central axis thereof;
   a plurality of fingers spaced along the length of the arm and substantially normal thereto in the direction of the first open end of the funnel-like member;
   the openings of the plurality of dialysis vessel means including an edge extending substantially parallel with but in the opposite direction of said fingers; and
   the edge of the opening of the one of said plurality of dialysis vessel means being disposed in the appropriate space defined between said fingers.

3. A device as described by claim 1, further including:
   strap means for attaching said capping means to said funnel-like member; and
   said strap means including a hinge section whereby the capping means is displaceable towards and away from the second open end of the funnel-like member.

4. A device as described by claim 3, wherein:
   the funnel-like member, the hanger means, the capping means and the strap means are integrally formed so as to provide a unitary device.

5. A dialysis device, comprising:
   a plurality of different-sized dialysis bag means for receiving dialysate, each of said bag means including an open end and a closed end;
   a plurality of dialysis vessel means for receiving said different-sized bag means, said plurality of vessel means including openings of different sizes, respectively;
   a hollow funnel-like member including a plurality of annular sections of different diameters coaxially connected to each other in order of progressing diameter, the annular section of smallest diameter defining a first open end and the annular section of greatest diameter defining an opposite second open end;
   each of the annular sections for disposition of a dialysis bag means of a different size thereon;
   the open end of the dialysis bag means of desired size being passed over the first open end of the funnel-like member and disposed on the annular section of appropriate diameter;
   means for securing the desired-size dialysis bag means disposed on the appropriate annular section to the funnel-like member;
   hanger means supported by the funnel-like member for suspending the funnel-like member from the opening of one of said plurality of dialysis vessel means, with the closed end of the dialysis bag means disposed thereon extending into the one vessel means;
   said hanger means including an arm supported by the funnel-like member adjacent the second open end thereof and extending substantially normal with respect to the central axis thereof, a plurality of fingers spaced along the length of the arm and substantially normal thereto in the direction of the first open end of the funnel-like member, the openings of the plurality of dialysis vessel means including an edge extending substantially parallel with but in the opposite direction of said fingers, and the edge of the opening of the one of said plurality of dialysis vessel means being disposed in the appropriate space defined between said fingers;
   means for capping the second end of the funnel-like member;
   strap means for attaching said capping means to said funnel-like member, said strap means including a hinge section whereby the capping means is displaceable towards and away from the second open end of the funnel-like member; and
   the funnel-like member, the hanger means, the capping means and the strap means being integrally formed so as to provide a unitary device.

6. A device as described by claim 5, wherein:
   each of the annular sections for disposition of a dialysis bag of a different size includes a plurality of exterior, radially projecting, circumferential rings in axially spaced relation to each other; and
   the open end of the dialysis bag means of desired size being passed over the first open end of the funnel-like member and disposed on the annular section of the appropriate diameter extending over one of the rings thereon.

* * * * *